US012679867B2

(12) United States Patent
Han et al.

(10) Patent No.: US 12,679,867 B2
(45) Date of Patent: Jul. 14, 2026

(54) POLYPEPTIDE FOR PREVENTING OR TREATING IDIOPATHIC PULMONARY FIBROSIS AND PHARMACEUTICAL COMPOSITION CONTAINING THE SAME

(71) Applicant: NEXEL CO., LTD., Seoul (KR)

(72) Inventors: Choongseong Han, Seoul (KR); Donghun Woo, Seoul (KR); Minkyung Kim, Seoul (KR); Junghyuck Park, Seongnam-si (KR); Joonchul Kim, Seoul (KR); Geunho An, Seoul (KR)

(73) Assignee: NEXEL CO., LTD., Seoul (KR)

( * ) Notice: Subject to any disclaimer, the term of this patent is extended or adjusted under 35 U.S.C. 154(b) by 714 days.

(21) Appl. No.: 18/015,975

(22) PCT Filed: Jun. 9, 2022

(86) PCT No.: PCT/KR2022/008103
§ 371 (c)(1),
(2) Date: Jan. 13, 2023

(87) PCT Pub. No.: WO2023/277376
PCT Pub. Date: Jan. 5, 2023

(65) Prior Publication Data
US 2024/0034751 A1     Feb. 1, 2024

(30) Foreign Application Priority Data
Jun. 28, 2021     (KR) ........................ 10-2021-0083762

(51) Int. Cl.
*C07K 7/06*          (2006.01)
*A61P 11/00*        (2006.01)

(52) U.S. Cl.
CPC ................ *C07K 7/06* (2013.01); *A61P 11/00* (2018.01)

(58) Field of Classification Search
CPC . C07K 7/06; A61P 11/00; A61P 43/00; A61K 38/1709; A61K 38/00
See application file for complete search history.

(56) References Cited

U.S. PATENT DOCUMENTS

| | | | |
|---|---|---|---|
| 10,266,578 | B2 | 4/2019 | Dubowchik et al. |
| 2017/0143785 | A1 | 5/2017 | Song |
| 2018/0230233 | A1 | 8/2018 | Chen et al. |
| 2018/0334486 | A1 | 11/2018 | Han et al. |
| 2021/0388041 | A1 | 12/2021 | Han et al. |

FOREIGN PATENT DOCUMENTS

| | | |
|---|---|---|
| KR | 10-1470793 B1 | 12/2014 |
| KR | 10-1845862 B1 | 4/2018 |
| KR | 10-2018-0126236 A | 11/2018 |
| KR | 10-2019-0115049 A | 10/2019 |
| KR | 10-2019-0129040 A | 11/2019 |
| KR | 10-2020-0046869 A | 5/2020 |

OTHER PUBLICATIONS

Daniel S Glass, Idiopathic pulmonary fibrosis: Current and future treatment, Clin Respir J . Feb. 2022; 16(2):84-96. doi: 10.1111/crj. 13466. Epub Jan. 10, 2022.*
Uniprot Protein Database, protein accession, Q08431 • MFGM_Human , Lactadherin—*Homo sapiens* (Human), accessed on Aug. 19, 2025.*
International Search Report for PCT/KR2022/008103 mailed Sep. 15, 2022 from Korean Intellectual Property Office.

* cited by examiner

*Primary Examiner* — Erinne R Dabkowski
(74) *Attorney, Agent, or Firm* — Revolution IP, PLLC

(57) ABSTRACT

The present invention provides a polypeptide for preventing or treating idiopathic pulmonary fibrosis, which is synthesized by linking 9 to 10 amino acids together and comprises an amino acid sequence consisting of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr). Accordingly, the polypeptide for preventing or treating idiopathic pulmonary fibrosis according to the present invention may restore lung function to normal by fundamentally treating lung tissue that has undergone fibrosis due to idiopathic pulmonary fibrosis, and furthermore, may delay or prevent the onset of idiopathic pulmonary fibrosis.

3 Claims, 4 Drawing Sheets

Specification includes a Sequence Listing.

POLYPEPTIDE FOR PREVENTING OR TREATING IDIOPATHIC PULMONARY FIBROSIS AND PHARMACEUTICAL COMPOSITION CONTAINING THE SAME

CROSS REFERENCE TO PRIOR APPLICATIONS

This application is a National Stage Application of PCT International Patent Application No. PCT/KR2022/008103 filed on Jun. 9, 2022, under 35 U.S.C. § 371, which claims priority to Korean Patent Application No. 10-2021-0083762 filed on Jun. 28, 2021, respectively, which are all hereby incorporated by reference in their entirety.

SEQUENCE LISTING

This application contains a Sequence Listing submitted via EFS-Web and hereby incorporated by reference in its entirety. The Sequence Listing is named SEQCRF_2405-013.txt, created on Dec. 12, 2025, and 1,360 bytes in size.

TECHNICAL FIELD

The present invention relates to a polypeptide for preventing or treating idiopathic pulmonary fibrosis and a pharmaceutical composition containing the same.

BACKGROUND ART

Idiopathic pulmonary fibrosis is a fatal disease in which inflammation occurs repeatedly in the lung interstitial tissue due to unknown causes and leads to permanent scarring and tissue fibrosis, which causes structural changes in the lung tissue, resulting in reduced lung function, leading to death.

This idiopathic pulmonary fibrosis is a rare disease for which the cause is unknown, and as the main symptom thereof, shortness of breath appears during exercise. As the symptoms progress, shortness of breath becomes more severe, and inflammation and fibrosis of the lungs stimulates the airways and lungs, leading to frequent dry cough.

Eventually, as shortness of breath becomes more severe, hypoxia may occur and a clubbing phenomenon may also occur in which the fingertips are rounded.

Currently, there is no drug approved as a direct therapeutic agent having a proven effect against idiopathic pulmonary fibrosis, but drugs such as Pirfenidone and nintedanib are being used for idiopathic pulmonary fibrosis, and these drugs have been proven to have the effect of delaying the progression of the disease, but have a limitation in that they cannot cure the disease.

In addition, prior art documents related to pharmaceutical compositions for treating idiopathic pulmonary fibrosis include Korean Patent No. 10-1845862 (entitled "Pharmaceutical composition for treating or preventing idiopathic pulmonary fibrosis") (hereinafter referred to as "conventional art").

However, pharmaceutical compositions for treating idiopathic pulmonary fibrosis, including the conventional, provide a partial therapeutic effect or an insignificant level of a therapeutic effect, and thus have a problem in that they cannot provide a fundamental effect of delaying the onset or progression of pulmonary fibrosis or treating pulmonary fibrosis.

DISCLOSURE

Technical Problem

The present invention has been made in order to solve the above problems, and an object of the present invention is to provide a polypeptide for preventing or treating idiopathic pulmonary fibrosis, which may restore lung function to normal by fundamentally treating lung tissue that has undergone fibrosis due to idiopathic pulmonary fibrosis, and furthermore, may delay or prevent the onset of idiopathic pulmonary fibrosis.

Technical Solution

To achieve the above object, a polypeptide for preventing or treating idiopathic pulmonary fibrosis according to the present invention is synthesized by linking 9 to 10 amino acids together and comprises an amino acid sequence consisting of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr).

Here, the polypeptide for preventing or treating idiopathic pulmonary fibrosis may be one of a first polypeptide consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-cysteine (C, Cys), a second polypeptide consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr), a third polypeptide consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-arginine (R, Arg), a fourth polypeptide consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-leucine (L, Leu), and a fifth polypeptide consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-lysine (K, Lys).

In addition, the polypeptide for preventing or treating idiopathic pulmonary fibrosis has a molecular weight of 1,035 to 1,200 Da, and the carboxy terminus (—COOH) of the amino acid sequence of the polypeptide for preventing or treating idiopathic pulmonary fibrosis may be converted into —$CONH_2$.

Furthermore, the polypeptide for preventing or treating idiopathic pulmonary fibrosis may reduce expression of at least one of collagen and α-smooth muscle actin (α-SMA) in a lung tissue to be prevented or treated.

In addition, the polypeptide for preventing or treating idiopathic pulmonary fibrosis may be formulated for intralesional administration or intratracheal administration.

Meanwhile, to achieve the above object, a pharmaceutical composition for preventing or treating idiopathic pulmonary fibrosis according to the present invention contains, as an active ingredient, the polypeptide for preventing or treating idiopathic pulmonary fibrosis having the above-described characteristics.

In addition, in another aspect to achieve the above object, the present invention provides a gene encoding the polypeptide for preventing or treating idiopathic pulmonary fibrosis having the above-described characteristics.

Advantageous Effects

The present invention has the following effects.

First, the polypeptide for preventing or treating idiopathic pulmonary fibrosis may provide the effect of alleviating idiopathic pulmonary fibrosis by exhibiting the effect of reducing the fibrosis index indicating idiopathic pulmonary fibrosis.

Second, the polypeptide for preventing or treating idiopathic pulmonary fibrosis may significantly reduce the expression level of collagen and α-smooth muscle actin (α-SMA), which is a marker of fibrosis of the lung tissue to be treated for idiopathic pulmonary fibrosis.

Third, it is possible to provide a polypeptide for preventing or treating idiopathic pulmonary fibrosis, which is biocompatible, has few side effects, and is easy to mass-produce and control for quality, and a pharmaceutical composition containing the same.

Fourth, the polypeptide for preventing or treating idiopathic pulmonary fibrosis may also be used to provide the effect of preventing or treating not only pulmonary fibrosis, but also similar diseases such as liver fibrosis and renal fibrosis.

MODE FOR INVENTION

Figure 1:
FIG. 1 is a schematic view showing a process for preparing experimental animal models designed to verify the effect of the polypeptide for preventing or treating idiopathic pulmonary fibrosis according to the present invention.

Preferred embodiments of the present invention will be described in more detail with reference to the accompanying drawings. In the following description, the description of already known technical features will be omitted or compressed for the sake of brevity of description.

1. Description of Polypeptide for Preventing or Treating Idiopathic Pulmonary Fibrosis A process for synthesis of a polypeptide for preventing or treating idiopathic pulmonary fibrosis according to the present invention and the structural characteristics of the synthesized polypeptide will be described in detail.

The polypeptide for preventing or treating idiopathic pulmonary fibrosis according to the present invention is a polypeptide synthesized by linking 9 amino acids together or a polypeptide synthesized by linking 10 amino acids together, according to implementation.

The polypeptide synthesized by linking 9 to 10 amino acids together according to each embodiment essentially comprises an amino acid sequence consisting of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr).

In other words, the polypeptide is based on an amino acid sequence of "RGDVFPSYT" (SEQ ID NO: 2), may have an RGD motif active region, and may further comprise one additional amino acid in the amino acid sequence itself or after the amino acid threonine (T, Thr) located at the very end.

Specifically, the present invention may provide a total of five embodiments, that is, first to fifth polypeptide forms. Although the amino acid sequences of the first to fifth polypeptides slightly differ from one another, the effects of these polypeptides on the prevention or treatment of idiopathic pulmonary fibrosis are sufficiently remarkable.

Specifically, the first polypeptide is a polypeptide having a "RGDVFPSYTC" (SEQ ID NO: 1) structure consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-cysteine (C, Cys), and has a molecular weight of 1,143 Da to 1,144 Da (most preferably 1,143.4 Da).

The second polypeptide is a polypeptide having a "RGDVFPSYT" (SEQ ID NO: 2) structure consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr), and has a molecular weight of 1,139 Da to 1,140 Da (most preferably 1,139.9 Da).

The third polypeptide is a polypeptide having a "RGDVFPSYTR" (SEQ ID NO: 3) structure consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-arginine (R, Arg), and has a molecular weight of 1,195 Da to 1,197 Da (most preferably 1,196 Da).

The fourth polypeptide is a polypeptide having a "RGDVFPSYTL" (SEQ ID NO: 4) structure consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-leucine (L, Leu), and has a molecular weight of 1,152 Da to 1,154 Da (most preferably 1,153 Da).

The fourth polypeptide is a polypeptide having a "RGDVFPSYTK" (SEQ ID NO: 5) structure consisting of an amino acid sequence of arginine (R, Arg)-glycine (G, Gly)-aspartic acid (D, Asp)-valine (V, Val)-phenylalanine (F, Phe)-proline (P, Pro)-serine (S, Ser)-tyrosine (Y, Tyr)-threonine (T, Thr)-lysine (K, Lys), and has a molecular weight of 1,168 Da to 1,169 Da (most preferably 1,168.2 Da).

Here, the polypeptide for preventing or treating idiopathic pulmonary fibrosis, which is one of the first to fifth polypeptides, is synthesized according to a predetermined sequence using a solid phase peptide synthesis method and has a purity of 90% or more.

The polypeptide for preventing or treating idiopathic pulmonary fibrosis, which is one of the first to fifth polypeptides and has been purified to have a purity of 90% or more as described above, has a molecular weight of 1,035 to 1,200 Da as determined by mass spectrometry. Check the molecular weight.

Furthermore, in order to increase the absorption of the polypeptide for preventing or treating idiopathic pulmonary fibrosis, which is one of the first to fifth polypeptides, the carboxy terminus (—COOH) of the amino acid sequence of the polypeptide for preventing or treating idiopathic pulmonary fibrosis may be converted into —CONH$_2$.

For example, the carboxy terminus (—COOH) corresponding to "C" for the first polypeptide, "T" for the second polypeptide, "R" for the third polypeptide, "L" for the fourth polypeptide, or "K" for the fifth polypeptide may be converted into "—CONH$_2$" to increase the absorption of the polypeptide.

The polypeptide for preventing or treating idiopathic pulmonary fibrosis of the present invention as described above may be used as a main active ingredient in a pharmaceutical composition used for preventing or treating idiopathic pulmonary fibrosis.

In addition, the polypeptide for preventing or treating idiopathic pulmonary fibrosis according to the present invention and a pharmaceutical composition containing the same as a main active ingredient may be formulated for intralesional administration, intratracheal administration, intravenous administration, or administration to a specific tissue (lung tissue).

2. Description of Results of Test for Verification of Polypeptide for Preventing or Treating Idiopathic Pulmonary Fibrosis In relation to the polypeptide for preventing or treating idiopathic pulmonary fibrosis according to the present invention, the effect of the polypeptide on the prevention or treatment of idiopathic pulmonary fibrosis was verified through a test, and the test was performed using the following experimental methods for the purpose of defining properties by means that are obvious to those skilled in the art.

(1) Preparation of Idiopathic Pulmonary Fibrosis Animal Models and Design of Experiment First, bleomycin was intratracheally instilled into 10 to 12-week ole C57BL/6 mice, thereby preparing acute idiopathic pulmonary fibrosis-induced animal models.

Specifically, 10-week-old C57BL/6 mice were anesthetized by mechanical ventilation with 2% isoflurane, and then the mouth of each anesthetized mouse was opened, the tongue was protruded as far forward as possible to make the airway visible, and then bleomycin, a pulmonary fibrosis inducer, was administered intratracheally at a dose of 2 mg/kg according to the standard (Methods Mol Biol. 2017; 1627:27-42).

Next, as shown in FIG. 1, after one week, idiopathic pulmonary fibrosis-induced animal model mice were selected randomly and divided into a PBS-instilled group (n=6) and a polypeptide-instilled group (n=6, 100 μg/kg), and 10-week-old C57BL/6 mouse models (n=5) in which idiopathic pulmonary fibrosis was not induced were classified as a vehicle-administered negative (NC) group (n=6) as a normal control group.

Here, for the PBS-instilled group (n=6) and the peptide-instilled group (n=6, 100 μg/kg), each of PBS and the polypeptide was administered intratracheally to the animals at a concentration of 100 μg/kg (Am J Respir Crit Care Med. 2001 June; 163(7):1660-8).

In addition, as the instilled polypeptide, each of the first to fifth polypeptides described above was instilled individually so that the test results could be compared between the polypeptides.

Specifically, in the groups instilled with the polypeptides, instillation of the first polypeptide is referred to as "NPT-0021", instillation of the second polypeptide is referred to as "NPT-0022", instillation with of the third polypeptide is referred to as "NPT-0023", instillation of the fourth polypeptide is referred to as "NPT-0024", and instillation of the fifth polypeptide is referred to as "NPT-0025".

Next, on day 3 after polypeptide instillation, the lung tissue was extracted as shown in FIG. 1 and histochemical analysis was performed as described below. Results of the evaluation and test methods to be described later are expressed as mean±SEM. For statistical significance, one-way ANOVA was used, and Scheffe's method was performed as a post hoc test.

(2) Evaluation of Ashcroft Score for Idiopathic Pulmonary Fibrosis Animal Models Evaluation was performed on the above-described three groups. However, for the peptide-instilled group, the first to fifth polypeptides were evaluated individually.

The animal models of each test group were anesthetized, and then the lung tissue was extracted therefrom. Immediately after extraction, one left lobe among five lobes of the lung tissue was stored in liquid nitrogen for protein extraction, and the remaining four lobes were cold-stored in 4% PFA (paraformaldehyde) solution for 1 day. Thereafter, paraffin blocks were prepared, cut into 20 μm-thick sections using a microtome (Leica), and attached to silane-coated slides.

The resulting lung tissue sections for each test group were deparaffinized with xylene, dehydrated, and then subjected to H&E staining using an H&E stain kit (hematoxylin and eosin) (ab245880).

Figure 2:
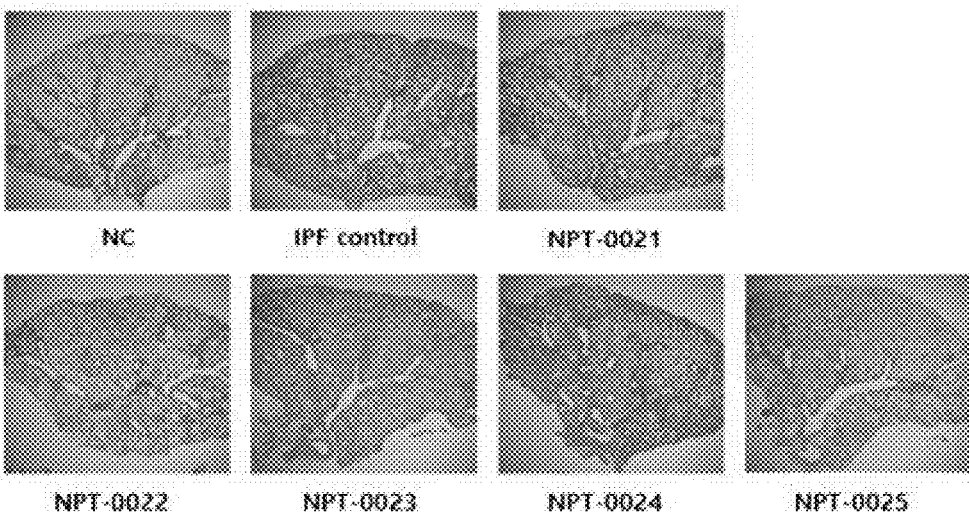
FIGS. 2 and 3 show the results of evaluating the Ashcroft score for the lung tissues of experimental animal models designed to verify the effect of the polypeptide for preventing or treating idiopathic pulmonary fibrosis according to the present invention.

Next, the samples were mounted on coverslips using a mounting solution. The stained tissue slides were observed under a microscope (NIKON), and the resulting images are shown in FIG. 2. In order to evaluate the inflammatory response in the lung tissue and the morphological characteristics and structural aspects of alveolar cells, immunohistochemical analysis was performed and the Ashcroft score was measured, and the results are in FIG. 3.

First, referring to FIG. 2, it is possible to compare the degree of fibrosis between the group (IPF control), to which PBS was administered intratracheally after induction of idiopathic pulmonary fibrosis, and the polypeptide-instilled groups (NPT-0021 to NPT-0025) into which each of the polypeptides was instilled intratracheally after induction of idiopathic pulmonary fibrosis.

As a result, it can be confirmed through FIG. 2 that the degree of fibrosis in all the peptide injection groups (NPT-0021 to NPT-0025), into which each of the polypeptides was instilled after induction of idiopathic pulmonary fibrosis induction, was statistically significantly alleviated.

Figure 3:
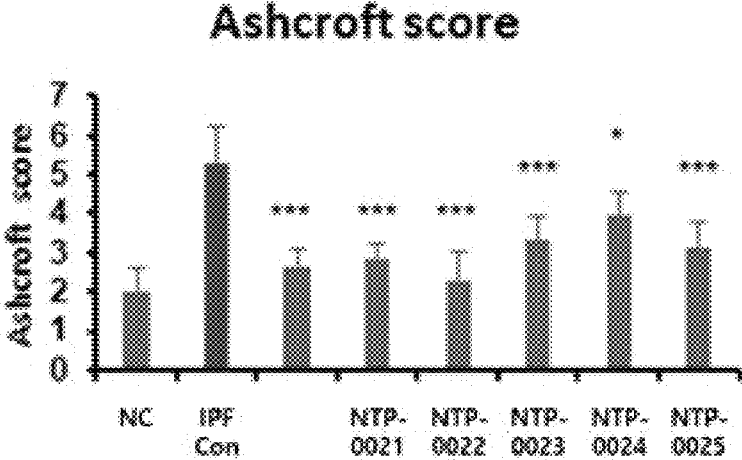

Referring to FIG. 3 showing the results of evaluating the Ashcroft score to numerically support the above finding, it can be confirmed that the Ashcroft score was lower in all the polypeptide-instilled groups (NPT-0021 to NPT-0025) than in the PBS-instilled group (n=6), and the degree of fibrosis was alleviated in the polypeptide-instilled groups (*** P<* P<0.05).

(3) Examination of Expression of Collagen and α-SMA in Idiopathic Pulmonary Fibrosis Animal Models Next, among all five lobes of the lung tissue extracted after anesthetizing the animal models of each test group, one left lobe stored in liquid nitrogen for protein extraction was cut, lysed, and analyzed by Western blotting. The results are shown in FIGS. 4 to 6.

Specifically, from the left lobe of the lung extracted from each animal of the group (IPF control), to which PBS was administered intratracheally after induction of idiopathic pulmonary fibrosis, and the polypeptide-instilled groups (NPT-0021 to NPT-0025) into which each of the polypeptides was instilled intratracheally after induction of idiopathic pulmonary fibrosis, protein was extracted using tissue lysis buffer, and the expression level of the representative marker alpha-smooth muscle actin (αSMA), which is increased upon fibrosis induction, was analyzed.

Figure 4:
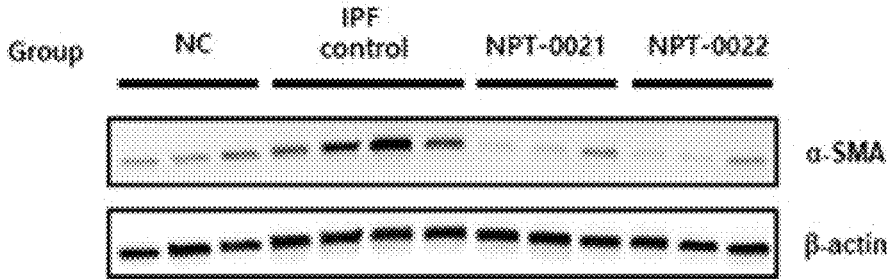
FIGS. 4 to 6 show the results of comparing changes in the expression pattern of α-SMA in the lung tissues of experimental animal models designed to verify the effect of the polypeptide for preventing or treating idiopathic pulmonary fibrosis according to the present invention.
Figure 5:
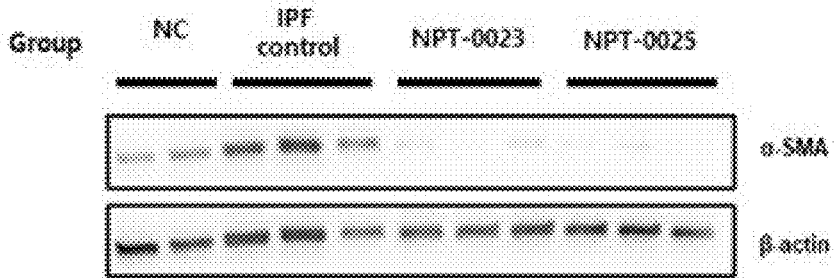
Figure 6:
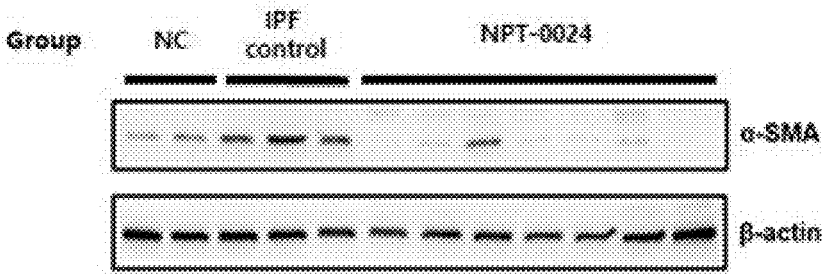

In fact, as shown in FIGS. 4 to 6, it could be confirmed that the expression level of αSMA was higher in the group (IPF control), to which PBS was administered intratracheally, than in the negative control (NC) group (n=6), and relatively decreased in all the polypeptide-instilled groups (NPT-0021 to NPT-0025).

In addition, among all five lobes of the lung tissue extracted after anesthetizing the animal models of each test group, the remaining four lobes excluding one left lobe stored in liquid nitrogen for protein extraction were cold-stored in 4% PFA (paraformaldehyde) solution for 1 days. Next, paraffin blocks were prepared, sectioned into 20 μm-thick sections using a microtome (Leica), attached to silane-coated slides, dehydrated, and then subjected to antigen retrieval and immunofluorescence staining to determine the expression level of collagen, and the results are shown in FIG. 7.

Furthermore, from the four lobes of each lung of the animal models of each test group, slides were prepared and analyzed using collagen antibody. The results of quantifying the expression level of collagen, which is a representative marker that increases upon fibrosis induction, in the lung tissue, are graphically shown in FIG. 8.

Figure 7:
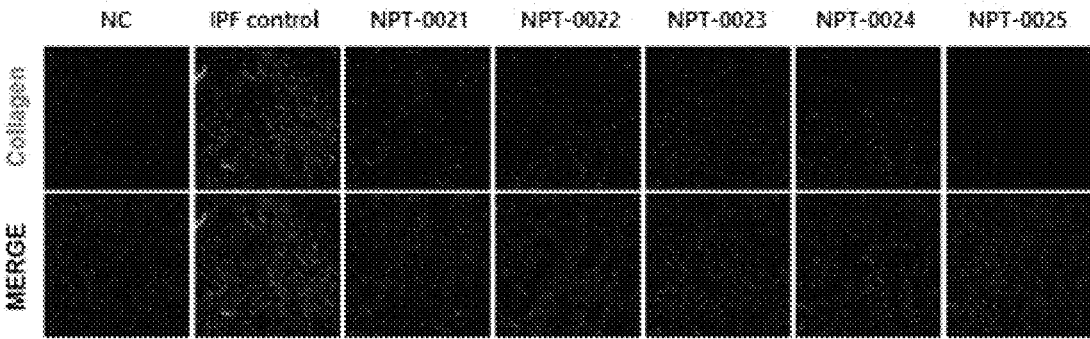
FIGS. 7 and 8 show the results of comparing changes in the expression pattern of collagen in the lung tissues of experimental animal models designed to verify the effect of the polypeptide for preventing or treating idiopathic pulmonary fibrosis according to the present invention.
Figure 8:
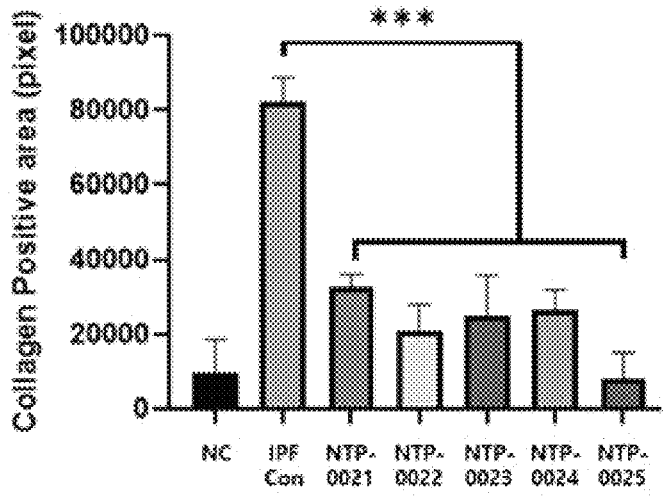

As a result, as shown in FIGS. 7 and 8, it could be confirmed that the expression level of collagen was higher in the PBS-instilled group (IPF control) than in the negative control (NC) group (n=6)), and rather decreased in all the polypeptide-instilled groups (NPT-0021 to NPT-0025).

In summary, the polypeptide for preventing or treating idiopathic pulmonary fibrosis according to the present invention is one of the first to fifth polypeptides. Accordingly, the polypeptide may reduce the Ashcroft score, which is an indicator of idiopathic pulmonary fibrosis, and may significantly reduce expression of collagen and α-smooth muscle actin (α-SMA), which are markers of fibrosis of lung tissue. Therefore, the polypeptide may restore lung function to normal by fundamentally treating lung tissue that has undergone fibrosis due to idiopathic pulmonary fibrosis, and furthermore, may delay or prevent the onset of idiopathic pulmonary fibrosis.

The embodiments disclosed in the present invention are not intended to limit the technical spirit of the present invention, but are intended to describe the invention, and the scope of the technical spirit of the present invention is not limited by these embodiments. The scope of protection should be construed by the appended claims, and all technical ideas within the scope equivalent thereto should be construed as being falling within the scope of the present invention.

---

The invention claimed is:

1. A polypeptide for treating idiopathic pulmonary fibrosis comprising an amino acid sequence selected from the group consisting of SEQ ID NO:1, SEQ ID NO:2, SEQ ID NO:3, SEQ ID NO:4 and SEQ ID NO:5, wherein the polypeptide is 9-10 amino acids in length, and wherein the carboxy terminus of the amino acid sequence is —CONH$_2$, wherein the polypeptide reduces expression of at least one of collagen and α-smooth muscle actin in lung tissue.

2. The polypeptide of claim 1, wherein the polypeptide is formulated for intralesional administration, intratracheal administration, or intravenous administration.

3. A pharmaceutical composition for treating idiopathic pulmonary fibrosis, comprising the polypeptide of claim 1 as an active ingredient.

* * * * *

SEQUENCE LISTING

```
<160> NUMBER OF SEQ ID NOS: 5

<210> SEQ ID NO 1
<211> LENGTH: 10
<212> TYPE: PRT
<213> ORGANISM: Artificial Sequence
<220> FEATURE:
<223> OTHER INFORMATION: synthetic construct

<400> SEQUENCE: 1

Arg Gly Asp Val Phe Pro Ser Tyr Thr Cys
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic construct

<400> SEQUENCE: 2

Arg Gly Asp Val Phe Pro Ser Tyr Thr
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Arg Gly Asp Val Phe Pro Ser Tyr Thr Arg
1               5                   10

<210> SEQ ID NO 4
<211> LENGTH: 10
<212> TYPE: PRT
```

-continued

```
<213> ORGANISM: Artificial Sequence
<220> FEATURE:
<223> OTHER INFORMATION: Synthetic construct

<400> SEQUENCE: 4

Arg Gly Asp Val Phe Pro Ser Tyr Thr Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Arg Gly Asp Val Phe Pro Ser Tyr Thr Lys
1               5                   10
```